(12) United States Patent
Winfrey

(10) Patent No.: US 7,361,197 B2
(45) Date of Patent: Apr. 22, 2008

(54) PROSTHETIC HAND HAVING A CONFORMAL, COMPLIANT GRIP AND OPPOSABLE, FUNCTIONAL THUMB

(76) Inventor: Rex Clayton Winfrey, 916 CR 702, Cleburne, TX (US) 76031

( * ) Notice: Subject to any disclaimer, the term of this patent is extended or adjusted under 35 U.S.C. 154(b) by 0 days.

(21) Appl. No.: 11/096,401

(22) Filed: Apr. 1, 2005

(65) Prior Publication Data
US 2006/0224249 A1    Oct. 5, 2006

(51) Int. Cl.
*A61F 2/54* (2006.01)
*A61F 2/68* (2006.01)
(52) U.S. Cl. ....................................... 623/64
(58) Field of Classification Search ............ 623/63, 623/64
See application file for complete search history.

(56) References Cited
U.S. PATENT DOCUMENTS

| | | | | |
|---|---|---|---|---|
| 1,929,926 A | * | 10/1933 | Laherty | 623/64 |
| 2,435,614 A | * | 2/1948 | Tureman, Jr. | 623/64 |
| 6,913,627 B2 | * | 7/2005 | Matsuda | 623/64 |

* cited by examiner

*Primary Examiner*—Bruce Snow

(57) ABSTRACT

An anthropomorphic artificial hand having a mechanical system that allows for the digits to be compliant to pressure that tends to flex the digits, and provides for the digits to be self biasing to conform to the shape of the object being grasped. The hand comprises one to four fingers, with the fingers having up to three joints each. The hand may also comprise a thumb that can be rotated into and out of opposition of the fingers. The joints of the thumb are also self biasing to allow conformance to the object being grasped. The hand is of the voluntary closing operation, with all digits being self extending. This allows the hand to use two cables to operate if body powered (one for the fingers, one for the thumb). The hand may also be electronically powered using two channels for operating the fingers and thumb simultaneously.

8 Claims, 5 Drawing Sheets

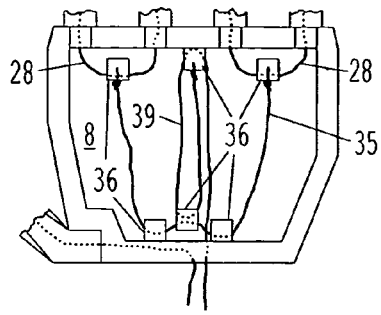
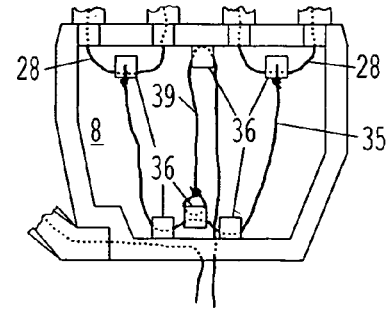
FIGURE 28  FIGURE 29
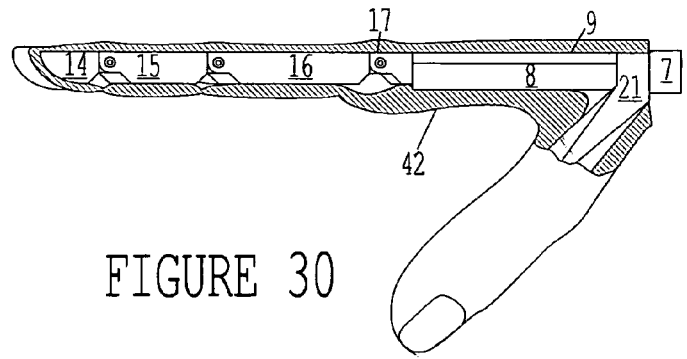
FIGURE 30
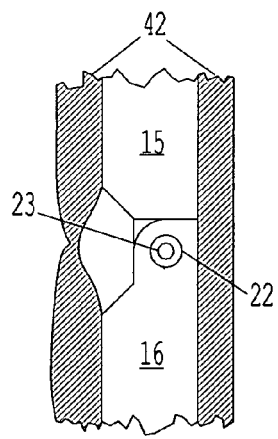 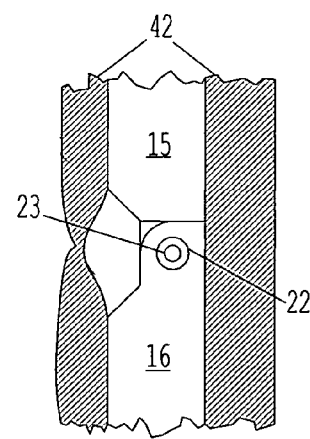 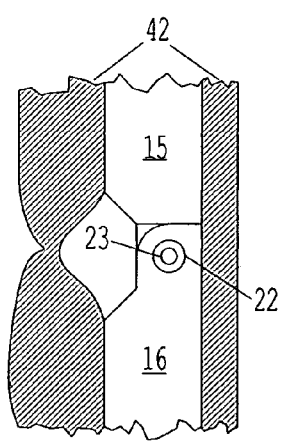
FIGURE 31  FIGURE 32  FIGURE 33

PROSTHETIC HAND HAVING A CONFORMAL, COMPLIANT GRIP AND OPPOSABLE, FUNCTIONAL THUMB

CROSS-REFERENCE TO RELATED APPLICATIONS

Not Applicable

STATEMENT REGARDING FEDERALLY SPONSORED RESEARCH OR DEVELOPMENT

Not Applicable

BACKGROUND OF THE INVENTION

This invention relates to a prosthetic hand and more specifically to an anthropomorphic hand providing for a conformal, compliant grip and having an opposable functional thumb. (This is the patent offices preferred method of description.)

From the time the first human survived an amputation, man has tried to make replacement body parts. The first replacement for an upper extremity amputation that seemed to be useful was the famous hook. It allowed the amputee to hold an object down, and pull it to them. If the object could be stabbed without ruining it, the amputee could pick up the object. The hook was slightly more useful than just using the stump.

The next successful prosthesis is the split hook. There have been many specific designs for the split hook, but they are functionally the same. Most are cable operated, and can be either voluntary opening, or voluntary closing. There have also been many methods of operation. U.S. Pat. No. 5,219,366 is an example of the split hook, with a novel operating system. U.S. Pat. No. 5,219,366 may look much different, but in basic terms is still a split hook. The split hook has an advantage over the hook in that the two halves of the hook can grasp an object and pick it up without having to resort to stabbing the object. Split hooks do allow a good view of the object being picked up. U.S. Pat. No. 5,219,366, while having several grasping surfaces, lost the 'good view' quality of the split hook. The biggest drawback to the split hook is the limited range that the hook can be opened in order to grasp an object. The split hook is not able to pick up a glass unless part of the hook is inserted into the glass, and whatever the glass contains. U.S. Pat. No. 4,149,278 is an example of the split hook that is operated by an electric motor. This patent also includes a 'wrist rotation' unit allowing the hook to be more easily aligned to the object being picked up. However it is still just a split hook. There have been the odd designs that could be termed the 'Swiss Army Knife' of the split hooks. These are still basic split hooks, though sometimes several split hooks in one unit. These numerous units would supposedly allow more usability. U.S. Pat. No. 4,332,038 is an example of such a 'multi-tool' design. These may gain a slight improvement in usefulness. However, they loose the advantage of the 'clear view of the object' allowed by the split hook. They also are so bazaar in appearance that very few amputees would ever consider using them in public.

Another variant that came from the split hook is the claw. U.S. Pat. No. 4,225,983 is an example of the claw design. The claw design usually has a wider opening range, allowing larger objects to be picked up. The shape also reaches around round objects to hold them. This prevents the object from slipping out of the wedge force exerted by a split hook. These also allow a good view of the object being picked up. They still have the same usability problems that the split hook has. Objects with a complex, or a tapered shape can not be held securely, and sometimes not at all. There have also been variants of the claw for specific purposes. One such is U.S. Pat. No. 5,163,966 for holding round bar materials. U.S. Pat. No. 4,377,305 is an example of the claw that is common for robotic use. This is virtually useless for prosthetics. The overall bulk of the claw would prevent most amputees from using it, and again, tapered objects can not be held securely. U.S. Pat. No. 4,990,162 is another example of the variations on the claw. This one in particular would probably damage most objects it attempts to pick up. The overall appearance would also keep most amputees from even considering it for use. U.S. Pat. No. 5,800,572 is a variation that has bigger drawbacks than most claws. There is no opposition contact possible with the two halves of the claw. The objects being picked up would have to be long enough to span all three 'fingers' of the claw to be picked up. U.S. Pat. No. 5,013,326 has the three 'fingers' spaced so that the single 'thumb' digit makes contact with both of the 'finger' digits. This design is in use in prosthetics for children. Like the others, it is very limited in what it is able to grasp.

The next progression in the anthropomorphic hand is fingers that flex at all the joints. This allows greater surface contact with an object being picked up. The force required to hold the object is reduced, reducing the battery power needed for electric hands, and less cable tension required by conventional (body powered) hands. U.S. Pat. No. 5,326,369 shows one method of bending jointed fingers. Driving a rotating force with a cable is a poor choice when the cable is bent while driving the force. The cables tend to develop torque induced twist that will cause the 'externally threaded cinctures' to bind in the bushings as well as the destruction of the cable. The sections of the fingers will also be moved in a given ratio to the others. The fingers will not be able to conform to the object being grasped. This will result in a small surface contact area being used for any object that does not perfectly fit into the designed curve of the fingers. This requires the force needed to grasp the object to be much higher, like that of a claw. U.S. Pat. No. 5,941,914 does not have the problem of the driving force causing binding, but the fingers are still locked into a designed curve of movement, with each section moving proportionally to the other sections. Again, unless the object just happens to fit that designed curve, more force is needed.

U.S. Pat. No. 4,094,016 shows a full hand, with flexing fingers. The thumb is built to also flex, but is locked into opposition of the fingers. Both the fingers and the thumb are positioned by the rotation of a single cam. The digits are also moved in a 'ratio' that gives a predetermined curve to the fingers. This again provides no conformability to objects. U.S. Pat. No. 4,364,593 shows a similar hand. This hand uses a complex linkage to operate the fingers. If the fingers do not make contact with the object at the same time, this linkage design will not allow for the torque loads that would be placed on parts 65 and 66. When the first finger makes contact, the forces can bind these two parts. There would only be a very small surface contact area being used to hold the object. This could easily damage those parts, and parts 17, 27, 37, 47, and 57. This would render the hand non-functional. This hand still functions as a claw.

U.S. Pat. No. 5,080,681 has some improvement in its ability to function. By using springs to extend the fingers, and a flexible substance to flex the fingers, the fingers are compliant to external forces that would tend to flex the fingers. The use of a flexible material for the 'tendons', will allow the fingers to flex at differing joints to conform to an object, but they will both have the same amount of total flex, which can prevent full contact with the object being grasped. The use of two tendons is actually useless, as the cable that operates one, operates the other in the exact amount. The 'first sliding actuating member' and the 'tendons' attached to it could be removed completely and the function of the hand would not be affected at all. No where in the description or claims, is there ever an explanation of how the sections work together to increase the functionality of the device. If there is a purpose for the second sliding member, and related tendons, the inventor forgot to include them, and an explanation of how it should work. This is a claw that has a slightly conformable grip.

U.S. Pat. No. 5,200,679 shows a hand that has conformability of the fingers. Unfortunately the fingers must either be operated by one motor, or by a motor for each finger. Using one motor, the hand would loose most of the conformability. This would occur when the first finger makes complete contact with the object being grasped. If separate motors are used for each finger, either complex control circuits must be built to allow each finger to continue to move until making contact, or several control channels would need to be used to control each finger separately. The other channels would have to be driven by separate myoelectric sensors, which is not plausible due to the limits of how many suitable sites can be found on the body that would not cause excessive cross talk interference between each channel. The cable system of this hand also has inherent problems. The fingers have no compliance to external forces that would cause the fingers to flex. The larger problem with the dual cable system has to do with excessive slack, or tension in the cables. Since one reel would be full and the other empty when the finger is fully flexed or extended, there is a difference in the movement of each cable, or each end of a single cable, for a given rotation of the shaft. This would either cause an excessive amount of slack, or tension in the cables. Excessive slack would allow the cables to slip off the reels, requiring the hand to need repair work. Excessive tension could cause damage to the cables, or the fingers, or the shaft and reels. This hand may well be usable for robotics, but is not satisfactory for prosthetics.

U.S. Pat. No. 4,986,723 also has the problem of too many control channels. It also has a very large number of parts that can fail, resulting in excessive maintenance. The cables are all kept under tension by springs. So they are less likely to come off the pulleys, but may slip on the pulleys, causing the sections of the fingers to get 'out of sync' with the other parts. This design also requires a large number of motors to operate it. Even if enough control channels were available for such prosthesis, the weight of the motors, and required power supply would prevent its use. On average, amputees will only tolerate prosthesis weighing less than 3.5 pounds. The motors alone would exceed that weight.

U.S. Pat. No. 5,080,682 has the problem also of too many motors needed to operate it, and the control channels needed to drive them. It also uses a flexible device (item 30) to push the digits into flexion. As it is easier to pull a chain than push it, this method of moving the fingers would fail, and be damaged at the slightest amount of pressure on the fingers. The 'push rod' (item 30) if flexible enough to bend around the fingers, would also be flexible enough to bend off line of its intended path, resulting in no movement of the finger, and possibly damage to the push rod. A flexible means of pushing a digit into flexion will structurally fail, but is completely acceptable to pull the digit into flexion.

U.S. Pat. No. 5,447,403 must be impressive in the lab, but will never exist as a functional prosthesis. It requires 16 servos to operate the hand, and 2 motors to operate the wrist. Again, there are too many control channels, and too much weight in the drive system. The hand would work well in a lab, or as part of a big, heavy robotic system.

U.S. Pat. No. 4,685,929 shows a voluntary closing hand that will function well. The thumb is adjustable to several positions, but is static while in use. The cable system is a good design, and the return spring system used to extend the fingers will work well. The fingers have compliance to external flexing forces, with out apparent damage happening. The fingers would each demonstrate a very slight degree of conformability. The design allows all fingers to be operated by one cable. The linkage has an offset to the lever moments to bias the strength to the first two fingers. A side effect of this will also allow a very slight amount of compliance in movement between the fingers, but very little before the linkage binds on itself. The lack of a functional thumb is a draw back. This hand, like many of the others, is still a nice looking claw.

BRIEF SUMMARY OF THE INVENTION

The human, and primate, hands have an opposable thumb. This is what sets them apart from other animals. The opposable thumb allows the use of two types of grasp. One is referred to as "pinch", and the other as "clutch". Pinch is moving the thumb in a manner that will pinch the object between the thumb, and the side of the first finger, as if holding a key. Clutch refers to holding an object between the tip of the thumb, and the tip of one or more fingers. There is not a single hand design that will function outside of a laboratory that allows the thumb to operate as the human thumb does. The human hand also complies with forces exerted on the fingers in such a manner as to flex them. Very few prosthetic hands have this ability. This compliance can be resisted in the human by intentionally extending the fingers against the force. Another property of the human hand is a conformal grip. This allows all fingers to flex individually to the point of contact with a multitude of shapes. There are no prosthetic hands that have this ability.

It is therefore an object of this invention to provide a prosthetic hand that has a thumb that is able to be moved into and out of opposition of the fingers by electrical or cable driven means.

It is further an object of the invention that said thumb can be flexed as a natural human thumb can be flexed to make contact with the fingers, driven by the same cable that causes opposition.

It is a further object of the invention that the thumb be able to make contact with the fingers as to provide both pinch and clutch methods of grasp.

It is a further object of the invention that the fingers be individually compliant to external forces exerted in such a manner as to flex the fingers.

It is a further object of the invention that this compliance will not cause the hand or fingers to malfunction in any manner.

It is a further object of the invention that the fingers have a conformal grip. This grip allows one or all fingers to fully close onto an object regardless of the position of the other fingers.

It is a further object of the invention that the conformability of the fingers be self-biasing.

It is a further object of the invention that this conformability of the fingers be a passive action of the function of the hand.

It is a further object of the invention that only one cable is needed for actuation of the four fingers.

BRIEF DESCRIPTION OF THE SEVERAL VIEWS OF THE DRAWINGS

FIG. 28 is a plan form view of the frame showing the final method used to route the cables for use by a recent amputee.

FIG. 29 is a plan form view of the frame showing the final routing of the cables for an experienced amputee.

FIG. 30 is an elevation view of a right hand from the medial side showing the outer glove partially cut away.

FIG. 31 is a partial view of a joint showing the relationship of the glove and the joint.

FIG. 32 is the same view as FIG. 31, with the dorsal side of the glove thickened to time the joint.

FIG. 33 is the same view as FIG. 31, with the palmer side of the glove thickened to time the joint.

DETAILED DESCRIPTION OF THE INVENTION

Figure 1:
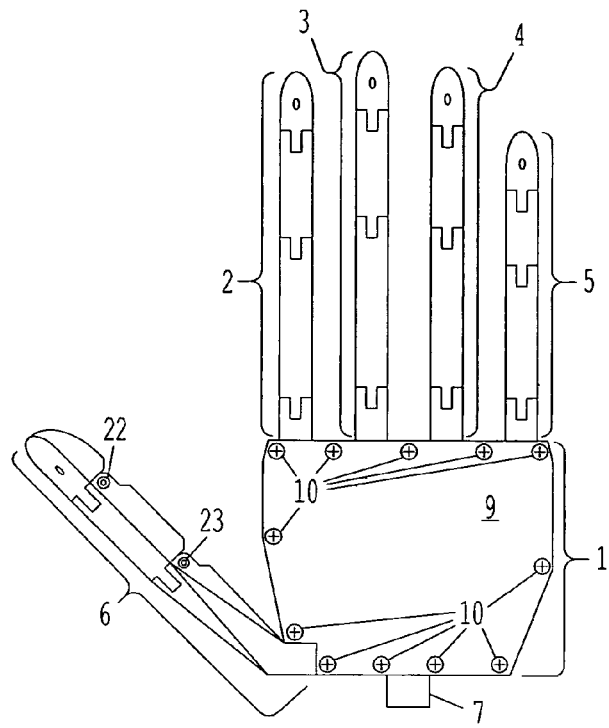
FIG. 1 shows the hand in plan form from the dorsal side

As seen in FIG. 1, the hand is made up of 7 distinct parts. Item 1 forms the frame of the hand. This frame (1) provides for the attachment of the fingers (2, 3, 4, 5), and the thumb (6). The frame (1) also contains the mechanism that allows the self biasing between the fingers (2-5), part of the hinge that allows opposition of the thumb (6), and the socket attachment point (7), allowing the amputee to wear the device. The attachment point (7) is a threaded piece of material that conforms to the standard attachment methods currently in use.

Figure 2:
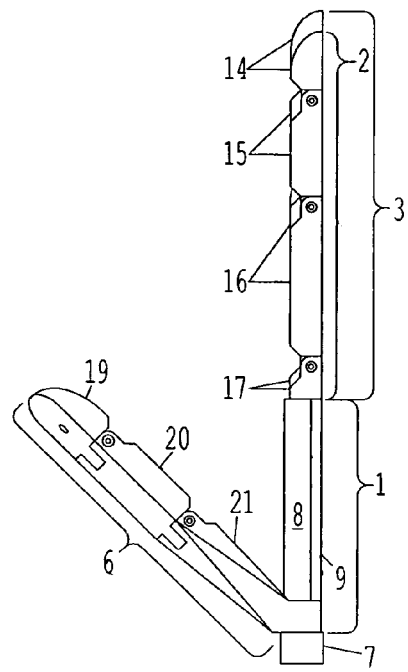
FIG. 2 show the hand in an elevation view from the thumb side. The thumb is rotated into the opposed position, with the fingers being extended.
Figure 3:
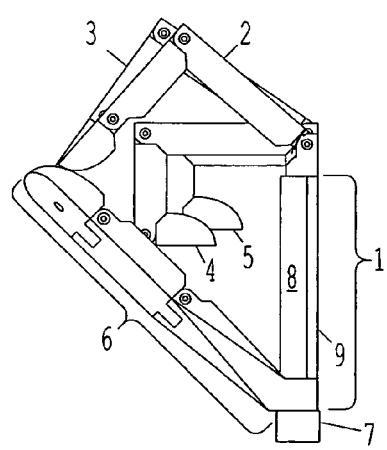
FIG. 3 shows the hand in a clutching position shown in elevation from the thumb side.
Figure 4:
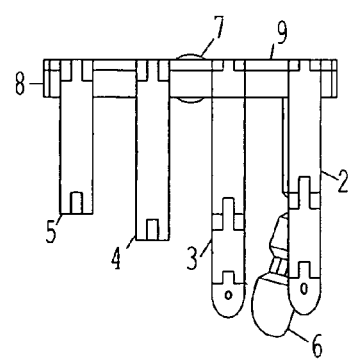
FIG. 4 shows the hand in the clutching position in an elevation view from the distal end.
Figure 5:
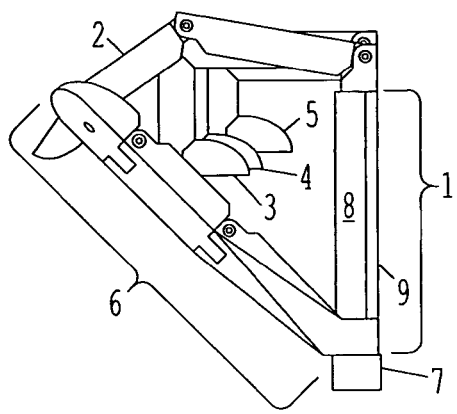
FIG. 5 shows the hand in the 'pinch' or 'key' position using an elevation view from the thumb side.
Figure 6:
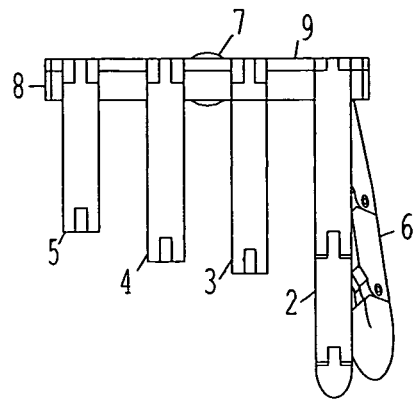
FIG. 6 shows the hand in the 'pinch', or 'key' position in an elevation view from the distal end.

The thumb (6) can be rotated in opposition to the fingers (2, 3, 4, 5) as seen in FIG. 2. The thumb (6) and fingers (2, 3, 4, 5) are self-biasing to allow conformal grip. This will be explained in detail in later paragraphs. FIGS. 3 and 4 show the hand in a "clutching" position. The thumb (6) is rotated into opposition to the fingers (2, 3, 4, 5), and flexed, and the fingers (2, 3, 4, 5) are flexed to make contact with the thumb (6). Due to the self-biasing between the fingers (2, 3, 4, 5), the first (2) and second (3) fingers are in contact with the thumb (6), and the third (4) and fourth (5) fingers are fully flexed against the palmer surface of the base. FIG. 5 and FIG. 6 show the hand in the pinching, or 'key' position. The fingers (2, 3, 4, 5) are flexed; the thumb (6) is then rotated until the tip makes contact with the first finger (2).

Figure 7:
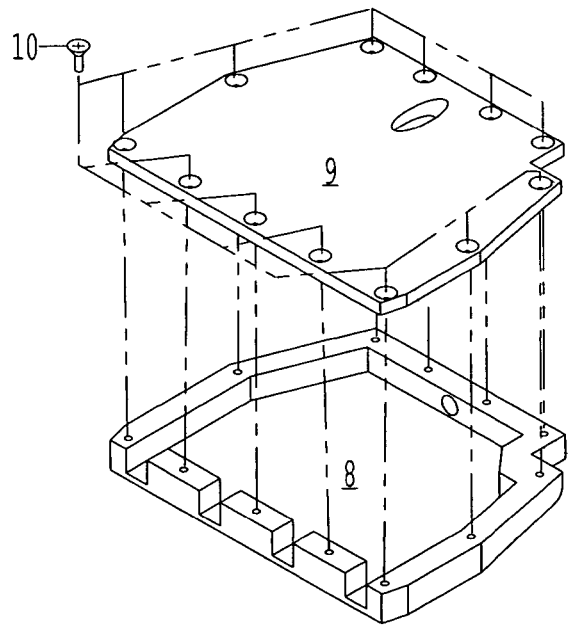
FIG. 7 is an exploded isometric view of the frame components.
Figure 8:
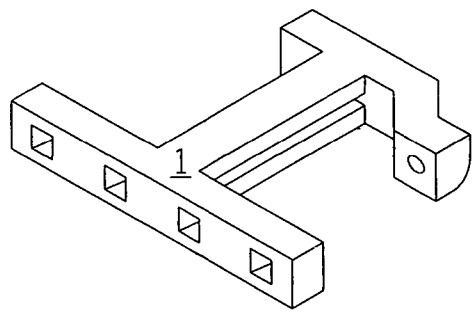
FIG. 8 is an isometric view of another method of building the frame.

The frame (1) of the hand used in the above figures represents one of many ways the frame (1) can be built. This version, shown in more detail in FIG. 7, is preferred for a body-powered version of the hand. The solid box design of frame (1) allows strength, rigidity, and a low weight. Screws (10) or other suitable fasteners so as to allow adjustment and repair of the hand attach the dorsal cover (9) to the main portion of the frame (8). The precise manner of construction is a matter of convenience to the manufacturer. This example uses a plate for the dorsal cover (9), and a machined block to form the main portion of the frame (8). The box may also be made up of several parts bonded to each other to achieve the same basic structure, or molded/cast as one part. This example can be formed of a lightweight material such as carbon (or fiberglass) composites, injection molded using 'glass filled plastics', or of metals, such as aluminum or titanium. Carbon composites would be preferred over fiberglass, as it will provide a stiffer, stronger frame with less weight. It is also preferred over metals for the same reason, but also for the added convenience of not setting off metal detectors as readily in such locations as airports, courthouses, etc. FIG. 8 shows one of many other possible configurations for the frame.

Figure 9:
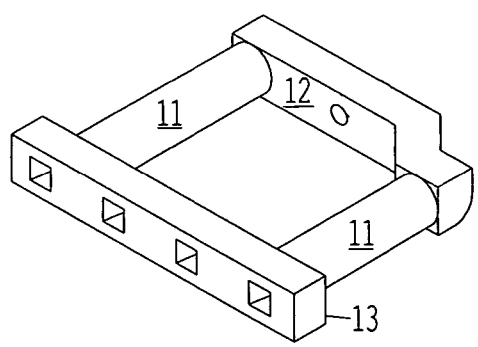
FIG. 9 is an isometric view of one method of building a frame for a motor operated hand.
Figure 10:
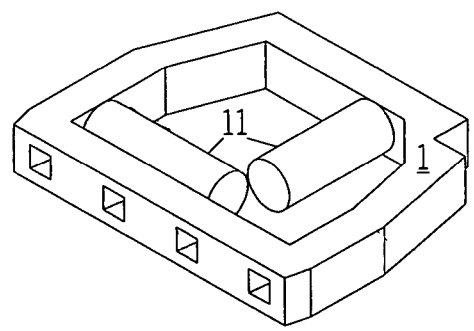
FIG. 10 is an isometric view of a second method of building a frame for a motor operated hand.

FIG. 9 and FIG. 10 show two of many possible configurations of the frame for use with electrically controlled hands. In FIG. 9, the motors (11) make up a structural part of the frame. The motors (11) drive the gearing and other mechanisms (not shown in detail for clarity) needed to operate the cables, these gearings and mechanisms being mounted within the proximal (12) and/or distal (13) ends of the frame. FIG. 10 has the motors (11) mounted within, or across open areas of the frame (1). In this embodiment, the motors are not a structural member.

Figure 11:
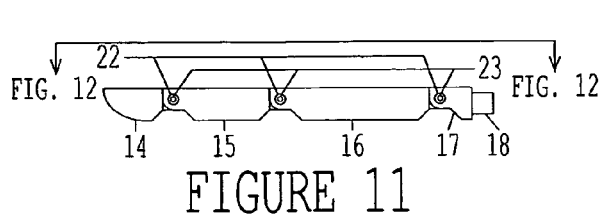
FIG. 11 is an elevation from the medial side of a finger showing the components of the finger.
Figure 12:
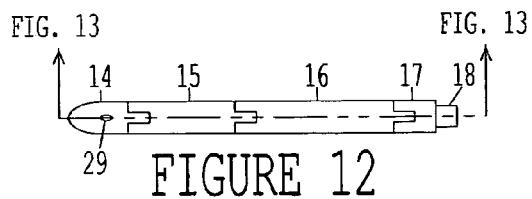
FIG. 12 is a plan form view of the finger shown in FIG. 11.
Figure 13:
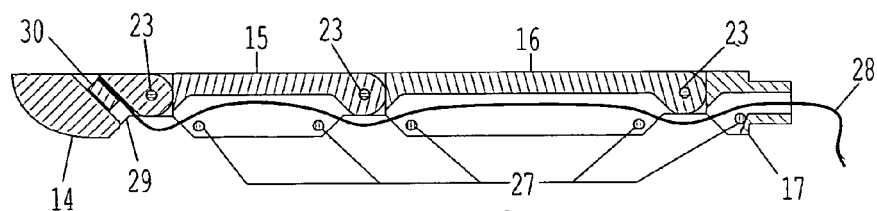
FIG. 13 is a cross section of a finger from the medial side.
Figure 14:
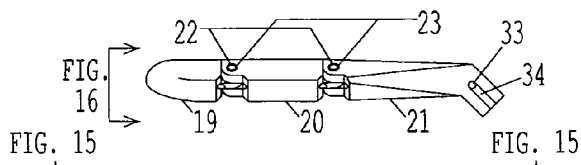
FIG. 14 is a plan form view of a right thumb from the palmer surface.

In FIGS. 11, 12 and 13 the fingers are shown as being made up of several components. In this embodiment, the components are machined from a solid material, such as aluminum, or preferably carbon composite. The components could be made from many other processes, such as laminated plates, or molded in shape by injection molding, or heat molding, even by way of extrusion. Four major components can be seen (14, 15, 16, 17). These correspond to the distal phalange (14), the medial phalange (15), the proximal phalange (16), and the distal end of the metacarpal (17), respectively, of the human fingers. The metacarpal (17) also has a portion (18) shaped to allow easy attachment to the frame (1) of the hand. In this embodiment, the attachment is made with an adhesive, such as epoxy, or cyanoacrylate. The thumb (6) is made up of three major components, two representing the proximal (20), and distal (19) phalanges, and one forming the entire metacarpal (21) as shown in FIG. 14. The components can be made of any combination of the materials that the frame can be made of, using any of the appropriate processes for those materials. The joints of the components are a simple hinge joint. The joints, for both the fingers and thumb, are comprised of a bushing (22) made of brass, bronze, or any other suitable material. Such materials such as engineering plastics may also be used, such as acetal, UHMW (Ultra-High Molecular Weight polyethylene), or PTFE (polytetrafluoroethylene). The hinge pins (23) can also be made of several materials. In this embodiment, the bushings (22) are brass, and the hinge pins (23) are made of hardened steel.

Figure 18:
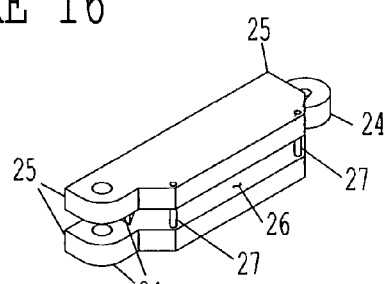
FIG. 18 is an isometric view from the distal, lower side of a phalange.
Figure 19:
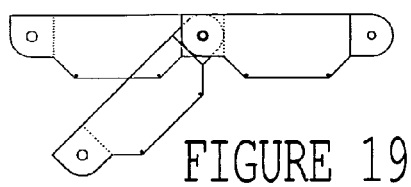
FIG. 19 is an elevation showing the function of the hyperextension stops, using a phantom image showing two positions of the medial phalange.

All of the proximal (16) and medial (15) phalanges have the same basic form, only differing in length. Likewise, all of the distal phalanges (14) are formed in the same basic shape as the others, only differing in size. FIG. 18 shows a medial phalange (15) in greater detail. The tongues (24) for the hinges are formed at each end. There is a stop face (25) at each end to prevent hyperextension of the joint. FIG. 19 shows how the stop faces (25) interact to prevent the hyperextension of the joint. The center of the phalange has a slot (26) running longitudinally to allow the terminal cable (28) to pass through the phalange. At each end of the slot there is a pin (27) that acts as part of the guide for the cable (28). This pin (27) holds the cable in place in the slot when the finger is flexed. This is shown in FIG. 13 in cross section. The position of the pins (27) in relation to the hinge pin (23) is important. By moving the pins (27) away from the hinge pin (23), the torque developed for a given pull on the cable increases, with an increase in the cable travel needed to fully actuate the joint, and conversely, as the distance to the hinge pin (23) is reduced, the strength decreases, with a reduction of the cable travel needed to fully flex the joint. The distance of these pins (27) to the hinge pins (23), can therefore be used to help 'time' the finger movement. By using slightly different pin (27) positions on each joint, the rate at which the fingers flex, and the force generated by each portion of the finger, in relation to each other can be adjusted, so as to reproduce the natural movement of the hand. The guide pin (27) should be made from a material that has enough strength to withstand the forces exerted by the terminal cable (28), and be smooth enough in surface finish to prevent abrasion of the terminal cable (28). In this embodiment a polished steel pin (27) is press fit into the phalange.

The distal phalanges are formed as seen in cross section in FIG. 11. The terminal cable (28) will pass into the hole (29) running longitudinally through the phalange (14) from the anterior surface to the dorsal surface. A headless screw (30) is then placed into the hole from the dorsal surface. The friction of the screw against the side of the hole and the cable holds the cable in place.

The fingers (2 through 5) are operated by terminal cables (28) running through them as shown in FIG. 13. These terminal cables (28) must be more flexible than the steel cables normally used. Steel cables can not be flexed in as small a radius as what is needed to bend the joints of the digits. There are several materials available that have the flexibility and strength needed to operate the digits, even with large loads placed on the digits. These materials include, but are not limited to aramide fibers, and variations of polyethylene, and polypropylene. Using the materials of this type, cables can be fashioned with the flexibility needed, small enough in diameter, and with a tensile strength in excess of 200 pounds. This is adequate for the functioning of the hand.

Figure 15:
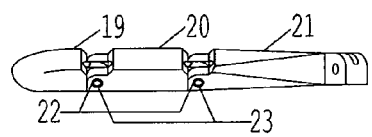
FIG. 15 is an elevation of a right thumb from the medial side.
Figure 16:
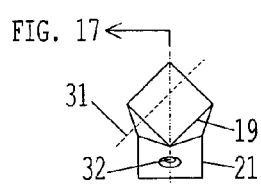
FIG. 16 is an elevation of a right thumb from the distal end, showing the relationship of the axis of the joints.
Figure 17:
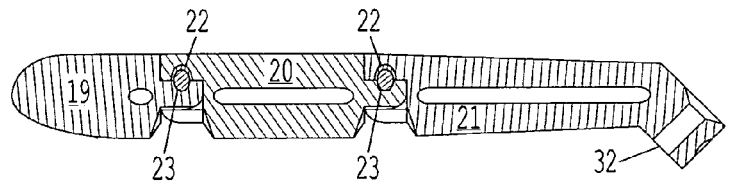
FIG. 17 is a cross section of a right thumb in plan form from the palmer surface.

The thumb (6) is shown in FIGS. 14, 15, 16 and 17. FIG. 16 shows the details of joint alignment in the metacarpal of the thumb (6). This drawing is for a right hand, as the left hand component would need to be a mirror image in order to cause the proper movement of the thumb (6). The axis of the metacarpal-phalange joint (31) is rotated approximately 45 degrees from the plane of the carpal-metacarpal joint (32). This approximates the alignment of the joint positions in the human hand. The terminal cable (28) for the thumb is routed through the center of the components, including the metacarpal. The terminal cable (28) exits the metacarpal through a hole (33) on the side slightly distal to the carpal-metacarpal joint. From there it is routed across a groove (34) in the exterior of the joint as shown in FIGS. 14 and 15. The cable therefore will pull the thumb into opposition, and flex the thumb. The carpal-metacarpal joint only provides movement in order to allow the thumb to be brought into opposition of the fingers. The joint does not allow abduction, or adduction of the metacarpal. The metacarpal is set to the most useful point of the range of abduction for the average hand, about 45 degrees from the axis of the second metacarpal as seen in FIG. 1. The carpal-metacarpal joint allows approximately 90 degrees of motion to move the thumb from the plane of the base of the hand into opposition of the fingers.

The control of which joint moves first is controlled by the return system, which will be discussed later. The joints are biased by the return system to allow the carpal-metacarpal joint to move first, at the lower tension, and the metacarpal-phalange, and phalange-phalange joint to move only after the tension of the cable increases. This increase will occur when the metacarpal has rotated either to the stop, or the point that part of the thumb has made contact with an object. The distal joints will then flex, each flexing until the distal component makes contact with the object being grasped. This allows the thumb to be moved into the appropriate amount of opposition, then create a conformal grasp, or make contact with the object if the object is located only at the tip of the thumb, such as the clutching position shown in FIG. 3 and FIG. 4.

Figure 20:
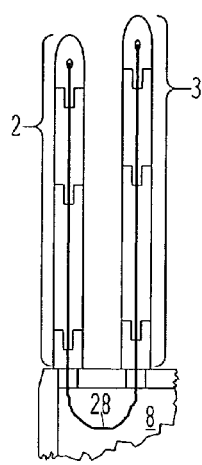
FIG. 20 is a plan form of the first two fingers, and part of the frame showing the method of attaching terminal cables.
Figure 21:
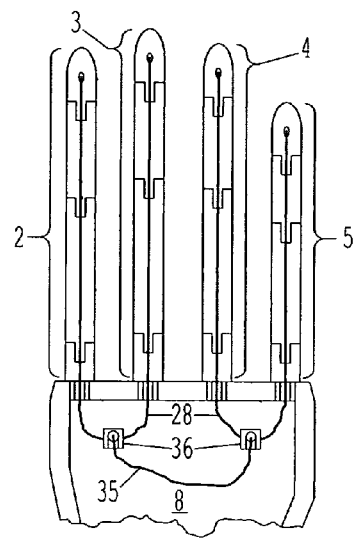
FIG. 21 is a plan form view of all four fingers and part of the frame showing both terminal cables in place.
Figure 22:
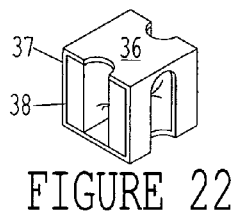
FIG. 22 is an isometric view of a slider block.
Figure 23:
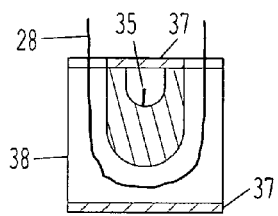
FIG. 23 is a cross section of a slider block.

The fingers themselves operate in a similar manner as the thumb. The cable allows each section of the fingers to flex according to; the tension of the cable, the compliance of the return system, and contact with the object being grasped. In order to allow the self-biasing of the fingers and only use one control cable, or motor, a passive biasing system must be used. This is accomplished by connecting two fingers (2, 3) together, by passing the terminal cable (28) from one fingertip through the finger, into the next finger and out though the fingertip of the second finger as shown in FIG. 20. When the loop extending from the pair of fingers is pulled, both fingers move. If the method of pulling the loop is such that the loop can slide through the point at which it is being pulled, each finger can move differing amounts, based upon the tension of the return system, and whether any part of the fingers make contact with an object. The return system will control the rate at which the fingers flex, therefore the fingers will move together, until the separate components of the fingers start to make contact with an object at which point only that part of the finger ceases to flex. In this way both fingers will continue to flex as the cable is pulled, until all parts of both fingers have made contact with the object being grasped, or they reach the end of the range of movement. Increasing tension on the cable at this point will cause the fingers to exert pressure. By running a terminal cable (28) through all four fingers (in pairs), the fingers are biased in pairs to allow a conformal grip. To bias the pairs to each other a biasing cable (35) is used. This cable is loosely attached to the terminal cables (28) by sliding blocks (36) as shown in FIG. 21. In this embodiment, the blocks are made up of a brass housing (37) containing a piece of engineering plastic (38) such as those mentioned earlier. In this case the material utilized is acteal for its high strength, high abrasion resistance, and self lubricating properties. The plastic (38) has a curved slot in which the cable runs, as seen in the cross section shown in FIG. 23.

Figure 24:
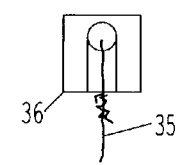
FIG. 24 is an elevation view of the attachment of a biasing cable of the slider block.

The biasing cable (35) can be attached to the sliding block (36) in several ways. The cable can also pass through the plastic block (38) and attached to itself, or be attached directly to the brass (37). In that the brass part is relatively small, it would be very easy for the edge of the brass to be sharp enough to cut, chafe, or otherwise damage the cable. In this embodiment, the cable is run through the block (36) and attached back onto itself as shown in FIG. 24. In this view, the cable has been tied securely to itself, then the knot saturated with cyanoacrylate adhesive. This adhesive sets very rapidly to form a crystal lattice structure that will prevent the knot from loosening. This is a common adhesive, also referred to as CA, Super Glue, Krazy Glue, and several other brand names. The exact chemical structure is not important to this invention, as long as the adhesive used can prevent the knot from loosening, other adhesives such as epoxy could also be used. In this embodiment, CA is used for its property of being easily dissolved by acetone; which makes it conducive to maintenance and repair.

Figure 25:
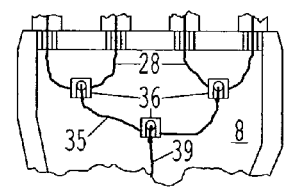
FIG. 25 is a plan form view of the frame showing the basic method of attaching all cables.
Figure 26:
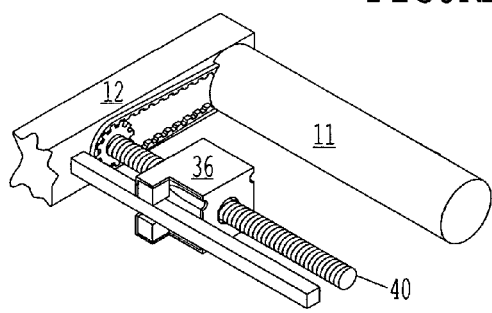
FIG. 26 is an isometric view of one method of using a motor to drive the fingers.
Figure 27:
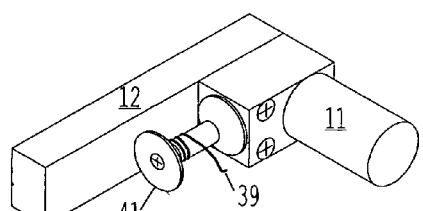
FIG. 27 is an isometric view of a second method of using a motor to drive the fingers.

The biasing cable (35) functions as the terminal cables (28) running through the fingers do. The cable functions by being allowed to slide through the point at which it is pulled. The pairs of fingers will be self biasing to each other, and each finger within the pairs will be self biasing. The actuating cable (39) by way of another sliding block (36) pulls the biasing cable (35), shown in FIG. 25. The actuating cable (39) is attached to the harness of the prosthesis allowing the amputee to actuate the hand. In an electrically driven version, the motor (11) can move the slide block (36) directly with a lead screw (40), or the actuating cable (39) may be wound upon a spool (41) by the movement of the motor (11). Variations of these methods are shown in FIGS. 26 and 27 respectively, note that these are not to be considered to be encompassing for all methods of actuating the biasing system, but are to show several other methods possible.

The operating cables have several essential features. The length of the cables needed to operate the biasing system is greater than the length of the frame of the hand. The cables can be passed through slider blocks (36) in order to reverse the direction of the movement. The actuating cable (39) can also be passed through slider blocks (36) in order to have the direction of pull arranged as needed to properly operate the biasing cable (35). The end of the actuation cable (39) can also be passed through the slider block (36) on the biasing cable (35) and returned in the direction from that it came, and anchored to the frame. This is shown in FIG. 28. This will increase the leverage of the actuating cable (39), allowing half the pressure needed by the amputee to operate the hand, but requiring twice the distance of movement to operate the hand.

The actuating cable (39) may pass out of the frame at any point that is convenient. The proximal wall, the palmer surface, or the dorsal surface can have an opening that will allow the cable to pass through. In this embodiment, the proximal wall of the frame base is used for convenience of illustration.

A new amputee normally does not have the strength in the muscles needed to develop very much pull on the cable. The amputee also will have to learn fine movement control of the cable to maximize dexterity of the hand. By increasing the travel needed by a factor of two, and reducing the force of pull needed by the same factor, the new amputee will be able to hold heavier objects, and have the control needed. After the amputee has developed the muscles involved, and learned control of the hand, the cable anchor point can be changed directly to the slide block, as shown in FIG. 29. This will reduce fatigue while using the hand since half the movement will be needed, and it will also allow faster actuation of the hand.

The conformal grip also reduces the amount of force needed to operate the hand. The increase in surface contact of the hand reduces the force needed to hold the object. This can be demonstrated by picking up a glass of water only using the tips of the thumb and two fingers, which requires more force than holding the glass of water with the palm, 4 fingers and the thumb.

The return system for the hand can be built in several ways. One would be to use torsion springs at each joint to extend the fingers. While this can be done, it increases the complexity of manufacturing the hand, and increases the number of parts than can fail. Another method would be to attach a stretchy material to the back of the digits. The material would stretch as each joint is flexed, and would return the joint to the extended position when the tension of the actuating cable is released. The stretchy material is also subject to friction across the joints, resulting in wear to the material. This results in the material wearing out quickly, and being difficult to repair or replace.

The covering of the hand assist in its functioning. Most of the newer hands produced use a cover over the mechanics to make the hand look like a hand. This cover is normally constructed of foamed PVC (polyvinylchloride). It has been noted in previous patents that the fingers grip better if the gripping surface is very soft, and better yet, using a material that exhibits hydrostatic pressure, such as a silicone gel. With silicones, there is no real defining line between a very soft solid, and a firm gel. The outer glove (42) for this invention would be preferably made of a very soft silicone. This glove (42) will also act as the return system for the hand. The glove will be molded into a position that will cause the fingers to return to the extended position when tension is released on the actuating cable. This is shown in FIG. 30.

The timing of the finger movement can be controlled by the thickness of the silicone on the anterior and posterior side of the joints. FIGS. 31, 32, and 33, show one joint with variations in the thickness of the glove (42). In FIG. 31 the glove is shown in a reference thickness for this example.

FIG. 32 shows the posterior wall of the glove (42) being thicker, which will cause the joint to bend less for a given tension. FIG. 33 shows the anterior wall thickened, which will have the same result, due to the compression when flexed. Using the anterior wall to control the timing of the fingers will also result in the object being grasped having an effect on the timing of the hand. Adjustments to the timing would be better controlled by only adjusting the posterior wall of the glove (42).

This method will allow the easiest repair of the return system when it becomes worn. With any other system, the glove would have to be removed in order to access any other return system. The gloves also become worn with time and use, and need replacement. Replacing the glove to take care of the upkeep of the return system would be a minor operation when it is needed, instead of further disassembly of the hand.

The foregoing description of the preferred embodiment of the invention has been presented for the purpose of illustrating the application of the basic properties of the invention. It is not intended to be exhaustive or to limit the invention to the precise form disclosed. As shown, many modifications and variations are possible in light of the above teaching. Those skilled in the arts will see many ways to utilize other materials, vary the size and shape of components, and use differing components to effect the same properties of function as falls with in the scope of the invention. It is intended that the scope of the invention be limited not by this detailed description, but rather by the claims appended hereto.

What I claim as my invention is:

1. An anthropomorphic prosthetic hand or robotic manipulator comprising:
    (a) a base section forming the major frame, representing the carpal carpal-metacarpal section of the human hand, onto, or into, which other components are mounted;
    (b) four individual digits appearing to be fingers attached to said frame, each having three joints allowing full, but not hyper-extension, individual movement of all joints;
    (c) one digit appearing to be a thumb attached to said frame having three joints, one of which represents the metacarpal-carpal joint and allows the thumb to rotate into and out of opposition of said fingers, with all joints allowing full, but not hyper-extension, individual movement;
    (d) a mounting point intended for the purpose of attaching said hand to the socket of the prosthetic system allowing donning of the device by the amputee;
    (e) two actuation systems mounted within said frame and extending into said digits, that causes said fingers to flex, or said thumb to rotate into opposition and flex, with the first system actuating said four fingers, the second system actuating said thumb such that said fingers and thumb can be operated separately, yet simultaneously, these actuation systems providing a passive, self biasing, conformal grip for said digits, which also provides for movement of the digits in the direction of flexure compliant to any external force without such movement causing any damage or malfunction of said digits, or actuation systems, with the actuation systems comprising a combination of highly flexible cables, and sliding blocks which allow the cables to be self biasing, and provide for changes in direction of force;
    (f) means to provide operating power for said actuation systems from outside of said hand;
    (g) a resilient device in the form of a glove to return the digits to the extended position by the use of compression and tension within the resilient material of said glove, which by variations in thickness in specific points of the resilient material also controls the timing of the movement of said joints in relation to each other to provide natural appearing movement of said hand.

2. The hand of claim 1 in which an activation system comprises a highly flexible flexion cable, one end of which being attached within the distal end of said thumb, passing through said thumb on the palmer sided of the distal two joints, then passing externally about the third joint, again on the palmer side, then passing into the frame of said hand, such that pulling the cable into said frame causes the thumb to flex, the second end of the cable thereafter being attached to the power source.

3. The hand of claim 1 in which an activation system comprising a series of highly flexible flexion cables arranged such that one flexion cable being attached at one end within the distal segment of one finger, runs through said finger on the palmer side of all joints, into said frame of said hand, into and through a second finger in the manner of the first finger, then being attached within the distal end of the second finger, a second flexion cable being run in like manner through the third and fourth fingers of said hand.

4. The hand of claim 3 further comprising a highly flexible intermediate cable attached to said first and second flexion cables such that one end of the intermediate cable is loosely attached to said first flexion cable at the portion creating a loop within said frame by use of a sliding block, allowing said first flexion cable to slide through the attachment point with little resistance, the second end of the intermediate cable being attached to second said flexion cable in a like manner, allowing second said flexion cable the same freedom of movement as the first flexion cable, the intermediate cable having a third mounting point consisting of a sliding block located so as to slide freely between the two end mounting points, this mounting point being used for the attachment to the power source.

5. The hand of claim 1 which further comprises two drive cables, each attached to one said actuation system such that pulling the cable away from said frame drives said actuation system, with the cables being powered by an energy source external to the hand, or prosthesis, the means to attach the cables to said energy source, the source of energy being the body of the amputee, with the method of actuation commonly being a harness worn by the amputee.

6. The hand of claim 1 which further comprises two motors driven by electrical means, each attached to one actuation system by means of direct ridged mechanical linkage, or by means of a flexible linkage such as a cable, the means to connect the motor(s) to a power source external to the hand, with the power source commonly being the motor control circuits operated by batteries.

7. The hand of claim 1 further comprising said resilient glove shaped so as to provide for the hand to appear to be a natural human hand, both in appearance, and to the touch.

8. The hand of claim 1 further comprising said resilient glove in which said resilient glove is made of such a material so as to provide a hydrostatic grip.

* * * * *